United States Patent [19]

Scaysbrook et al.

[11] Patent Number: 5,142,918

[45] Date of Patent: Sep. 1, 1992

[54] APPARATUS TO MEASURE THE BENDING LENGTH AND BENDING RIGIDITY OF FABRICS

[75] Inventors: Frank Scaysbrook, Epping; Nhan G. Ly, Baulkham Hills, both of Australia

[73] Assignee: Commonwealth Scientific & Industrial Research Organization, Campbell, Australia

[21] Appl. No.: 548,909

[22] PCT Filed: Jan. 31, 1989

[86] PCT No.: PCT/AU89/00031

§ 371 Date: Aug. 15, 1990

§ 102(e) Date: Aug. 15, 1990

[87] PCT Pub. No.: WO89/07267

PCT Pub. Date: Aug. 10, 1989

[30] Foreign Application Priority Data

Feb. 5, 1988 [AU] Australia ............................... PI6610

[51] Int. Cl.⁵ .............................................. G01N 3/20
[52] U.S. Cl. .......................................... 73/854; 356/129
[58] Field of Search ................. 356/429, 431; 250/560, 250/561, 562, 563; 73/789, 849, 159, 7, 857, 769, 854

[56] References Cited

U.S. PATENT DOCUMENTS 3,933,035 1/1976 Bobst et al. ............................ 73/769
4,247,204 1/1981 Merlen et al. ...................... 356/431

Primary Examiner—Vincent P. McGraw
Assistant Examiner—LaCharles P. Keese
Attorney, Agent, or Firm—Ladas & Parry

[57] ABSTRACT

An apparatus to measure the bending length and bending rigidity of a piece of fabric comprising a generally planar surface upon which the plate of fabric is moved. The surface terminates at one end with an edge over which a leading end of the fabric passes. An optical device defines a plane extending downwardly from the surface edge at approximately 41.5 degrees. The optical device detects when the plane is intersected by the leading end of the fabric when, after a sufficient length of the piece of fabric has passed beyond the surface edge to cause bending of the fabric piece, the leading edge of the fabric intersects the plane.

5 Claims, 2 Drawing Sheets

APPARATUS TO MEASURE THE BENDING LENGTH AND BENDING RIGIDITY OF FABRICS

BACKGROUND OF THE INVENTION

The present invention relates to apparatus to measure the bending length and bending rigidity of fabric.

PRIOR ART

The recent introduction to the garment manufacturing industry of sophisticated instruments for measuring fabric mechanical and physical properties has raised the awareness of the textile industry to the usefulness of objective measurement for quality control and product development. However, apart from being expensive, the currently available instruments require a skillful and devoted operator. These are the main reasons for the reluctance of most tailors to adopt fabric objective measurement for quality control.

OBJECT OF THE INVENTION

It is the object of the present invention to overcome or substantially ameliorate the above disadvantages.

SUMMARY OF THE INVENTION

There is disclosed herein an apparatus to measure the bending length and bending rigidity of fabrics, said apparatus comprising:
a generally horizontal planar surface terminating at one end with an edge, upon which a strip of fabric is placed and along which it is moved, a distance transducer mounted adjacent said surface to detect the distance moved by said strip;
a detector to determine when a leading edge of said strip passes the edge of said surface; and
an optical sensor to detect when said leading edge intersects a plane extending downwardly from said surface edge at an acute angle to the horizontal.

DESCRIPTION OF THE PREFERRED EMBODIMENT

Figure 1:
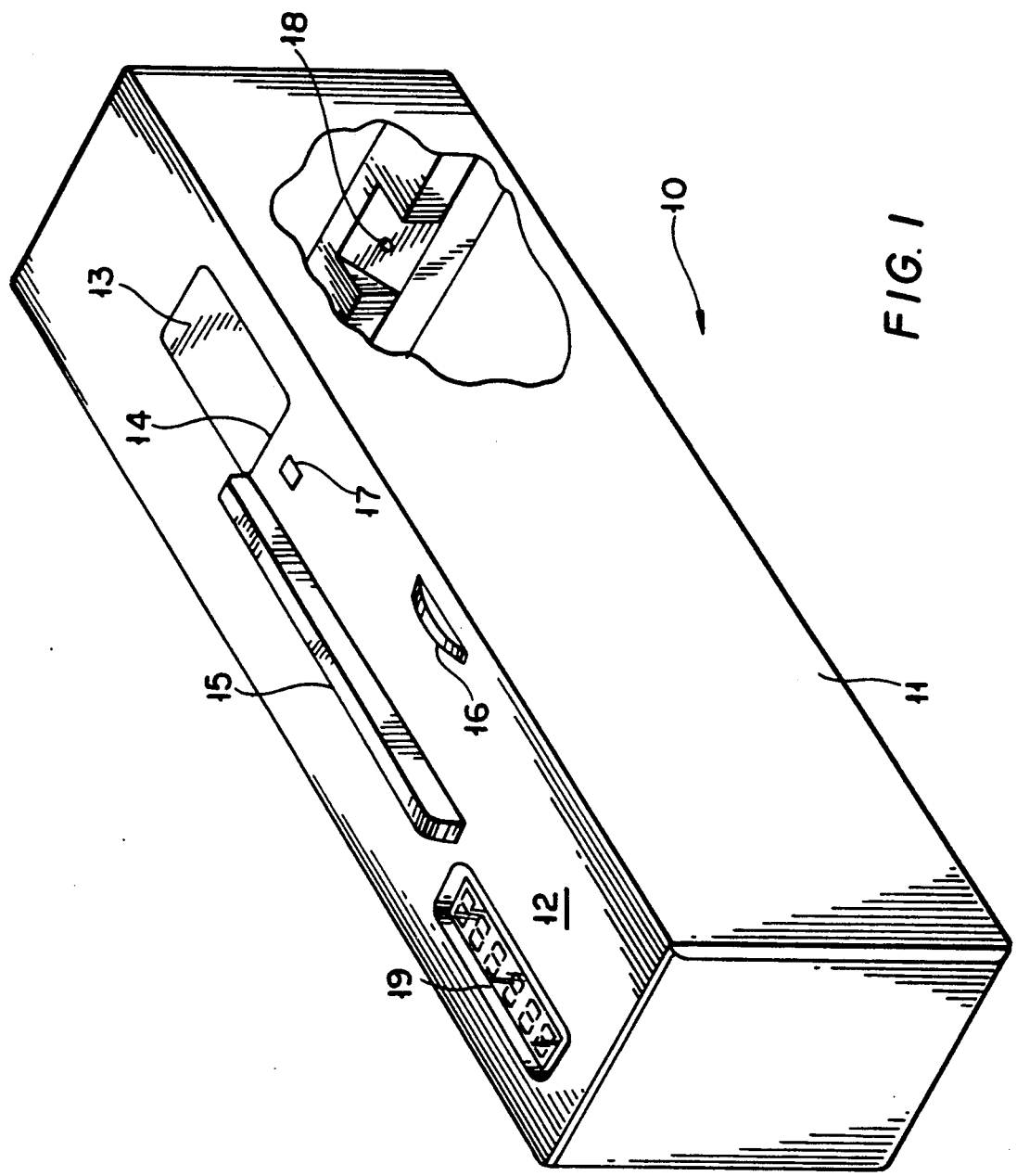
FIG. 1 is a schematic, perspective view of a measurement apparatus according to this invention.

A preferred form of the present invention will now be described by way of example with reference to the accompanying drawing, which schematically depicts in perspective view an apparatus to measure the bending length and bending rigidity of fabric.

In the accompanying drawing there is schematically depicted an apparatus 10 (flexometer) to measure the bending length and bending rigidity of fabrics.

The apparatus 10 includes a body 11 having an upper horizontal surface 12 provided with an aperture 13 having a straight edge 14. Extending in a direction generally normal to the edge 14 is a guide bar 15 along which a length of fabric is moved toward the edge 14.

Mounted adjacent the surface 12 is a displacement transducer 16 which measures the distance travelled by the fabric strip. Located adjacent the edge 14 is a reflective sensor 17 to determine when the leading edge of the strip passes thereby.

Mounted within the body 11 is a photodetector 18 which detects when the leading edge of the strip intersects a plane extending downwardly from the edge 14 at an acute angle of between 40° and 45°, preferably about 41.5°, to the horizontal.

A digital readout 19 shows the length of the fabric extending between the edge 14 and the point of intersection with the leading edge of the fabric with the above-mentioned plane.

The above apparatus 10 measures two bending properties of a fabric, that is the fabric bending length which is related to the ability to drape a material, and the fabric bending rigidity which is related to the quality of stiffness when a fabric is handled. The bending rigidity is particularly critical in the tailoring of lightweight fabrics as a very flexible fabric (low bending rigidity) may cause seam puckering while a high bending rigidity fabric can be more manageable in sewing and produce a flat seam.

A photodetector 18 is used to detect the point where the overhanging part of a rectangular strip of fabric bends and reaches a plane inclined at 41.5° to the horizontal. The bending length (LB) is displayed automatically with the use of an electronic encoder, thus the error due to the operator's judgement is eliminated. This bending legth is combined with the cloth mass M (g/cm$^2$) to give the fabric bending rigidity (B) as shown in the following relations:

$$B = 0.10M\ LB3(mg.cm)$$

Figure 2:
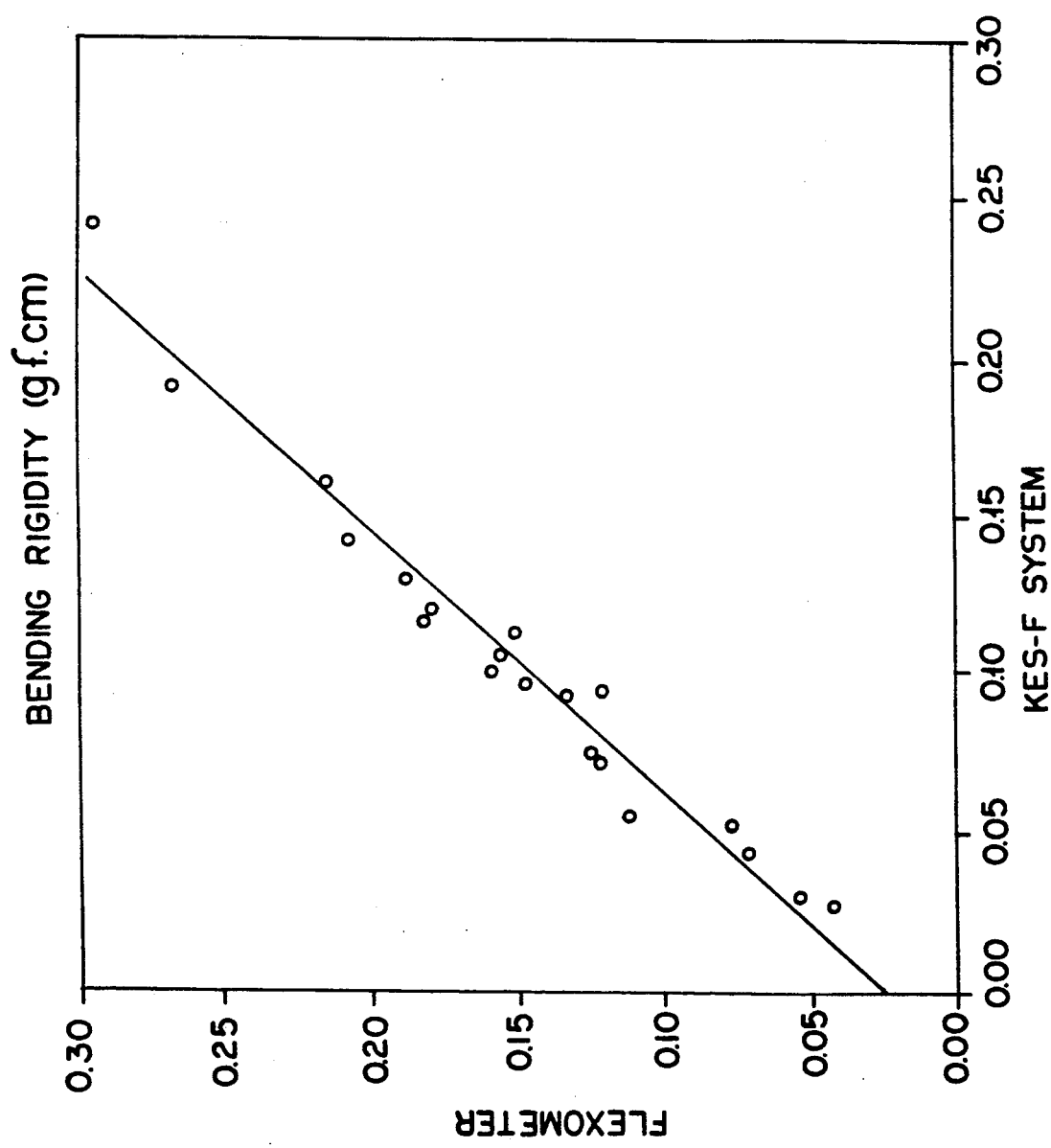
FIG. 2 is a graph showing the correlation in measurements of bending rigidity made with an apparatus according to the present invention and measurements made with a known KES-F Bending Tester.

Initial measurements with the apparatus 10 show good correlation in the bending rigidity between this instrument and the KES-F Bending Tester A correlation coefficient of 0.98 was found for 10 worsted fabrics covering a variation in fabric weight from 113 g/m$^2$ to 453 g/m$^2$, both warp and weft directions were measured. This is shown in the FIG. 2. Despite the high correlation, the KES-F values are significantly lower than those given by the Stiffness Meter. This is because measurements were done on the KES-F Bending Tester prior to the modification of the instrument's clamps by the manufacturer which raises the measured bending rigidities to values approximately equivalent to the apparatus 10.

We claim:

1. An apparatus to measure the bending length and bending rigidity of fabrics, said apparatus comprising:
a generally horizontal planar surface terminating at one end with an edge, upon which surface a strip of fabric is placed and along which it is moved, a distance transducer mounted adjacent to said surface to detect the distance moved by said strip;
a detector to determine when a leading edge of said strip passes the edge of said surface; and
an optical sensor to detect when said leading edge intersects a plane extending downwardly from said surface edge at an acute angle to the horizontal.

2. The apparatus of claim 1 wherein said angle is between 40° and 45°.

3. The apparatus of claim 2 wherein said angle is approximately 41.5°.

4. The apparatus of claim 3 further including means to define a linear path along which the fabric is moved towards said surface edge.

5. The apparatus of claim 3 wherein said distance transducer is a displacement transducer.

* * * * *